United States Patent [19]

Nakanishi et al.

[11] Patent Number: 5,296,223

[45] Date of Patent: Mar. 22, 1994

[54] SUBTILISIN AS AN ORAL THROMBOLYTIC AGENT

[75] Inventors: Koichiro Nakanishi, Kobe; Hajime Hiratani, Osaka; Kazuo Kato, Kobe, all of Japan

[73] Assignee: JCR Pharmaceuticals Co., Ltd., Hyogo, Japan

[21] Appl. No.: 960,259

[22] Filed: Oct. 13, 1992

Related U.S. Application Data

[63] Continuation of Ser. No. 616,904, Nov. 21, 1990, abandoned.

[30] Foreign Application Priority Data

Nov. 24, 1989 [JP] Japan .................................. 64-305868

[51] Int. Cl.$^5$ ............................................. A61K 37/547
[52] U.S. Cl. ................................. 424/94.64; 435/222
[58] Field of Search ..................... 424/94.64; 435/222

[56] References Cited

PUBLICATIONS

Rudenskaya et al., BA85:89212, 1987.
Magda et al., Acta Phys. Acad Sci Hung 44 (3/4) 1975.

*Primary Examiner*—Douglas W. Robinson
*Assistant Examiner*—Jean C. Witz
*Attorney, Agent, or Firm*—Burgess, Ryan & Wayne

[57] ABSTRACT

There are provided thrombolytic agents suited for oral administration. The agent comprises a proteolytic enzyme of subtilisin family, such as subtilisin BPN', subtilisin Carsberg, subtilisin amylosacchariticus, etc., produced by microorganisms belonging to genus Bacillus, such as *Bacillus subtilis, Bacillus licheniformis, Bacillus amyloliquefaciens*, etc. and, even when administered orally, exhibits thrombolytic activity.

6 Claims, 2 Drawing Sheets

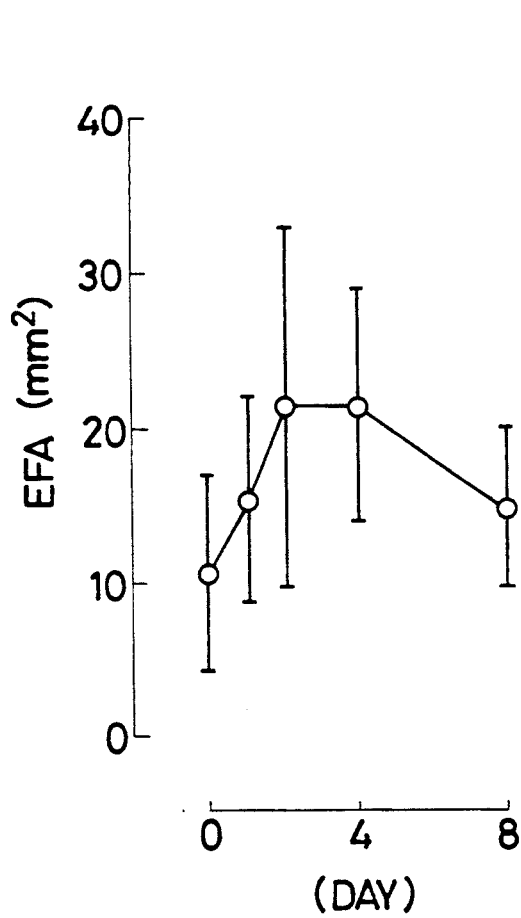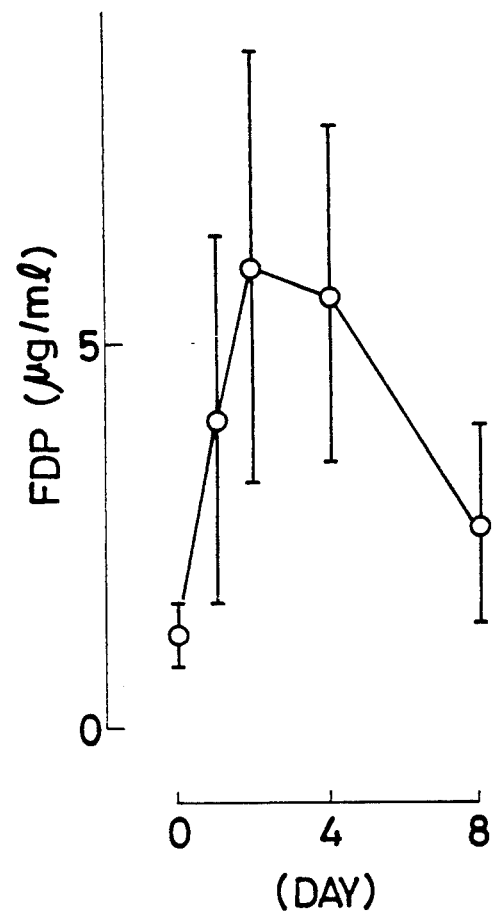

SUBTILISIN AS AN ORAL THROMBOLYTIC AGENT

This application is a continuation of application Ser. No. 616,904, filed Nov. 21, 1990, abandoned.

BACKGROUND OF THE INVENTION

This invention relates to thrombolytic agents for oral administration, which contains as an active ingredient a proteolytic enzyme of the subtilisin family being produced by a microorganism of the genus Bacillus, such as *Bacillus subtilis, Bacillus amyloliquefaciens* and *Bacillus licheniformis.*

DESCRIPTION OF THE RELATED ART

A thrombus is closely associated with various diseases, such as peripheral arteriovenous thrombosis, pulmonary embolism, myocardial infarction, coronary embolism, cerebral embolism and retinal arteriovenous thrombolism, and presents a grave problem as an pathogenic factor. For the treatment of thrombotic diseases, at present, fibrinolytic therapy has been often employed mainly with use of streptokinase (hereinafter referred to briefly as "SK") in Western Europe and United States of America and urokinase (hereinafter referred to briefly as "UK") in Japan. Recently, it has become known that the plasminogen activator, as obtained from the cells of melanoma, one of the human malignant tumors, possesses the same amino acid sequence as the enzyme called the tissue plasminogen activator (hereinafter referred to briefly as "TPA") being produced into the blood by the human angioendothelial cells. The said TPA, with its stronger affinity than UK for fibrin being attributed to the formation of thrombi, is considered to be highly effective against thrombotic diseases, and clinical application studies have already been completed with TPA that is produced not only by the human melanoma cells but also by microorganisms through genetic engineering. TPA has been marketed in the United States of America, whereas such product is still in the stage of clinical trials, with investigation being under way on modified TPA having part of the amino acid sequence changed. Such kinds of TPA are needed for clinical trials in larger quantities than initially anticipated, and are now encountering difficulties due to increased prices in relation to limited production amounts.

SK is a kind of foreign matter to the human body, and when repeatedly given humans through intravenous injection, incurs the risk of causing a variety of allergic reactions. Since UK and TPA both show half-lives in the living body as short as 30 min or less after intravenous injection and are inhibited by different inhibitors in the blood, resulting in loss of their activities, furthermore, such sophisticated techniques as infusion of large maintenance doses are required. However, large-dose administration of these drugs brings about the risk of enhanced tendency toward bleeding as a side effect. Once, there was developed a fibrinolytic enzyme for oral administration, or UK for oral administration. Oral administration of enteric coated capsules containing the UK was observed to cause the endogenous plasminogen activator to be released into the blood (Robbins et al., "Urokinase", Basic on Clinical Aspects, pp. 265 (1982). Published by Academic Press). In practice, such oral UK preparations once were put into clinical trials and were confirmed to be effective (Abe et al., "blood and Vessel", 12, 342 (1981)). However, they have never been brought into clinical use, because UK has already been commercially available in the form of intravenous preparation and has found pertinent application, while the oral UK preparations had to be administered at fairly greater doses, resulting in difficulties encountered in securing the larger production amounts.

This invention is intended to overcome such problems and also to provide a thrombolytic agent for oral administration that can be made available at a comparatively cheap price in larger quantities.

SUMMARY OF THE INVENTION

UK and TPA, as put heretofore into clinical use for the fibrinolytic therapy are known to act as an enzyme capable of dissolving fibrin plates, and such a fact has led to the utilization of these enzymes as a pharmaceutical. The present inventors as well have conducted intensive research so far on UK and a variety of microbial cultivation products and in the course of this, noticed that the protcolytic enzymes produced by microorganisms of the genus Bacillus, which are easily obtainable for example through cultivation, such as subtilisin BPN', subtilisin Carsberg and subtilisin amylosaccharyticus being produced by *Bacillus subtilis, Bacillus licheniformis* and *Bacillus amyloliquesiens*, respectively, can develop fibrinolytic activity in the screening test (the fibrin plate method) for fibrin clot dissolving activity. The research, followed by further investigation, has led the present inventors to the finding that the proteolytic enzymes derived from the Bacillus microorganisms, which the present inventors have discovered, can demonstrate fibrinolytic activity even in the absence of plasminogen, whereas UK needs plasminogen to elicit its fibrinolytic activity. The above-described enzymes produced by the Bacillus microorganisms, which the present invention is concerned with, are already known as a proteolytic enzyme, but have been found by the present inventors to demonstrate novel action and to be utilized in new application fields, and the finding has culminated into the present invention.

DESCRIPTION OF THE PREFERRED EMBODIMENTS

Figures 1, 2, 3:
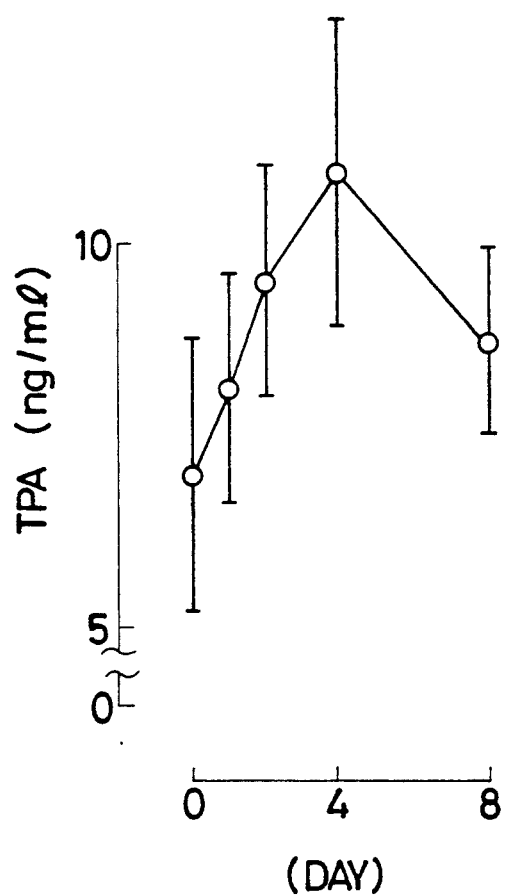

The present invention is concerned with thrombolytic agents for oral administration which contain the proteolytic enzymes of the subtilisin family being produced by micro-organisms of the genus Bacillus.

As the proteolytic enzyme of the subtilisin family, there may be mentioned, for example, subtilisin BPN', subtilisin Carsberg and subtilisin amylosacchariticus.

Subtilisin BPN', an enzyme produced by *Bacillus subtilis*, is referred to as nagase or subtilopeptidase and has already been commercialized. The present inventors found that use can be made of either the commercial product of the enzyme after being purified to an increased degree of purity through Butyl Sepharose gel-permeation chromatography or a culture product of *Bacillus subtilis* after being purified in accordance with the method of Hagihara et al (J. Biochemistry, 45, 185 (1958)), followed by the treatment in the manner similar to the commercial product. As subtilisin Carlsberg which has been made commercially product available, there may be used either of the commercial product after being purified furthermore through gel-permeation chromatography or a culture product of *Bacillus licheniformis* after being purified through the procedure of A. V. Guntelberg et al. (Comp. Rend. Lab. Carlsberg, Ser. Chim., 29, 36 (1954)), followed by purification by gel-permeation chromatography. With reference to subtilisin amyloloquesiens, or an enzyme produced by *Bacillus amylosaccharoticus*, there may be employed a cultivation product of *Bacillus amylosaccharoticus* after being purified through the method of D. Tsuruta et al. (Agr. Biochem., 30, 1261 (1966)), followed by further purification by use of Butyl Sepharose gel-permeation chromatography.

According to ATCC (American Type Culture Collection), *Bacillus mesentericus* is contained in the species *Bacillus licheniformis*, and *Bacillus licheniformis* in this invention includes *Bacillus mesentericus*.

The enzymes as being exemplified in the above are already known, with their characteristic properties being clarified; given in "Biochemical Data Book" edited by the Biochemical Society of Japan is the description that subtilisin BPN' shows a molecular weight of 27.5 kd and an isoelectric point of 7.8 and subtilisin Carsberg has a molecular weight of 27.3 Kd and an isoelectric point of 9.4, while subtilisin amylosaccharitcus exhibits a molecular weight of 27.5 Kd and an isoelectric point of 7.8.

The purified enzymes having the said characteristic properties as obtained by the above procedures can be used in the form of dried or concentrated product through drying under reduced pressure or lyophilization. However, the proteolytic enzymes according to this invention are not of human origin, and unlike UK of human origin, their intravenous administration for fibrinolytic therapy possibly brings about antigen-antibody reactions and involves a highly grave risk. In view of these, the present inventors conducted a great diversity of investigation with the varied methods of administration for the proteins. Oral administration is the least burdening and troubling to patients but is generally considered not to permit proteins given orally to migrate into the blood. The present inventors also realize well the fact but entirely contrary to their expectation, found that the proteolytic enzymes according to this invention, when given orally for the confirmation of this, give rise to intensification of the fibrinolysis activation system in the blood. Although the mechanism of action for such enzymes canot at present be explained completely, it cannot be denied that the post-administration intensification of the tissue plaminogen activator activation in the blood is related to the effects of the orally given proteolytic enzymes of this invention. The dosage amount can be varied according to the degree of purification of the enzymes of the present invention, whereupon it is the most desirable to use the commercially available enzymes according to this invention after being purified to such an extent as may possibly be administered to humans.

The enzymes of this invention as employed in the assessment of the effect after oral administration was assayed for purity by means of casein hydrolysis capacity; namely, the peptides, formed by hydrolyzing casein with the enzyme at 37° C. and pH 7.5, were allowed to produce a color with Folin's reagent, and the purity was determined through the coloration, whereby the amount of the enzyme showing the coloration corresponding to 1 micromol of tyrosine for the 1 min period was taken as a unit.

Referring to the drawings, FIG. 1-1, FIG. 1-2 and FIG. 1-3 are graphs showing the time-course changes of the blood EFA, FDP and TPA levels in relation to a number of days elapsed after administration of subtilisin Carsberg.

It is desirable to administer the enzyme of this invention in the form of enteric-coated preparation, in order to prevent decomposition of the enzyme before absorption. The enteric-coated preparation can be produced by the known procedures, for example, by providing powders or granules containing the enzyme with enteric coating or filling them into enteric-coated capsules. With reference to the amount of the enzyme being contained in such pharmaceutical preparation, a wide range of selection can be allowed (from 0.02 to 2 g per human adult), and the enzyme is desirably administered at a daily dose of 0.05 to 1 g, as divided in once to three times. Described below are the experiment examples and examples to illustrate this invention more specifically.

EXPERIMENT EXAMPLE 1

Fibrinolytic activity by the fibrin plate method (T. Astrup and S. Mullertz, Archs. Biochem. Biophys., 40, 346–351 (1952)):

Subtilisin BPN' (type XXVII) manufactured by Sigma Co., subtilisin Carsberg (type VIII) and subtilisin amylosaccharitcus as obtained by the procedure described in Example 1 were dissolved in deionized water, individually, to prepare their respective, aquepous solutions of 100, 50 and 25 μg/ml concentrations. Each of the sample solutions was place on a fibrin plate and warmed for 18 hours at 37° C., followed by measurement of the dissolved area (mm$^2$) of the fibrin membrane. In this experiment, two kidns of the fibrin plates were prepared and used; namely, one was the fibrinogen type I of bovine origin manufactured by Dai-Ichi Kagaku Yakuhin Co. of Japan, Tokyo, which was used as a standard plate (+Plg) and the other the fibrinogen type II of bovine origin manufactured by the same company, which was utilized as a plasminogen-free plate (−Plg), while thrombin used was of bovine origin manufactured by Mochida Pharmaceutical Co. of Japan. In this experiment, urokinase (produced by our own company) and plasmin (supplied by Sigma Co.) were employed as a control enzyme. The results are shown in Table 1, which indicates evidently that the proteolytic enzymes of the subtilisin family exhibit fibrinolytic activity, thereby leading to the finding that such proteolytic enzymes demonstrate fibrinolytic activity without the need of mediating the activation of plasminogen to plasmin.

The mode of action as shown by the enzymes of this invention is evidently different from the one of UK, but display the same tendency as plasmin; nonetheless, it is obvious that the enzymes of this invention differ in mode of action from plasmin, as well.

The evaluation results, as tabulated in Table 1, are based on the test procedure of utilizing fibrin clots attributed to the thrombus formation in the living body which were prepared experimentally in the laboratory, and prove that the proteolytic enzymes of the subtilisin family develop proteolytic activity.

TABLE 1

| Fibrinolytic activities of the proteolytic enzymes of the subtilisin family | | | |
|---|---|---|---|
| | | Lyzed area, mm$^2$ | |
| Enzyme | Concn. μg/ml | Standard plate +Plg | −Plg plate −Plg |
| Plasmin | 1,500 | 183.0 | 182.3 |

TABLE 1-continued

Fibrinolytic activities of the proteolytic enzymes of the subtilisin family

| Enzyme | Concn. μg/ml | Lyzed area, mm² Standard plate +Plg | −Plg plate −Plg |
|---|---|---|---|
| | 750 | 144.6 | 141.1 |
| | 375 | 114.5 | 109.3 |
| | 100 | 55.6 | 48.3 |
| | 50 | 39.4 | 27.9 |
| | 25 | 25.0 | 20.5 |
| UK | 100 | 727.8 | 0 |
| | 50 | 660.5 | 0 |
| | 25 | 606.4 | 0 |
| | 0.1 | 178.9 | 0 |
| | 0.05 | 124.5 | 0 |
| | 0.025 | 95.0 | 0 |
| BPN' | 100 | 335.9 | 348.8 |
| | 50 | 255.2 | 261.6 |
| | 25 | 196.7 | 190.5 |
| | 12.5 | 130.6 | 132.9 |
| Carlsberg | 100 | 337.7 | 352.7 |
| | 50 | 267.4 | 272.3 |
| | 25 | 200.9 | 211.7 |
| | 12.5 | 127.2 | 139.8 |
| Amylosacchariticus | 100 | 324.0 | 327.6 |
| | 50 | 252.8 | 251.2 |
| | 25 | 200.2 | 194.6 |
| | 12.5 | 130.0 | 131.1 |

A 40 g quantity of subtilisin BPN' (produced by Sigma Co.) was dissolved in 1,000 ml of 0.01M phosphate buffer of pH 7.0 containing 1.5M ammonium sulfate, and the solution was poured for adsorption into a column of 1,000 ml of Butyl Sepharose (produced by Pharmacia Co.) equilibrated in advance with the same buffer. Then, the column was washed thoroughly with the same buffer as used for equilibration and elution was effected with 300 ml of 0.01M phosphate buffer of pH 7.0 not containing ammonium sulfate to give 35 g of the purified product. Furthermore, 35 g of the product was subjected several times to gel-permeation chromatography on a column (5 cm°×90 cm) of Sephadex G-100 equilibrated with 0.05M phosphate buffer of pH 7.0 containing 1% of sodium chloride, and elution was performed with the same buffer to give 32 g of the purified product.

The thus purified subtilisin BPN' was filled in 0.05 g portions into enteric-coated capsules to conduct the application experiment; the enteric-coated capsules were given five human adults orally at the daily dose of 3 capsules, as divided in three times, for the period of 8 days, and blood samples were drawn from each of the adult volunteers in the time-course manner to determine changes in blood fibrinolytic activity Namely, the whole blood clot lysis times (hereinafter referred to briefly as "WCLT") were measured in accordance with the procedure of Chohan et al. [I. S. Chochan et al.: Thrombo. Diathes. Haemorrh. (Stuttg), 33, 226–229 (1975)], according to which 0.2 ml of the blood sample was admixed with 1.7 ml of 0.12M sodium acetate (pH 7.4) and 0.1 ml of thrombin solution (50 units, thrombin used was as produced by Mochida Pharmaceuticals Co. of Japan), followed by measurement of the length of time required for the dissolution of fibrin clots formed at 37° C.; the fibrinolysis activity (EFA) of the eurogloburin fraction was determined with use of the method of Kluft et al. [C. Kluft et al.: Progress in Chemical Fibrinolysis and Thrombolysis, 2, 57–65, J. F. Dabidson et al. (ed), Reven Press, New York (1976)]; namely, a precipitate (eurogloburin fraction) formed by adjusting to pH 5.9 a blood sample diluted 10 fold with distilled water was dissolved in EDTA buffer, and 0.03 ml of the solution was placed on the standard fibrin plate (T. Astrup and S. Mullertz, Archs. Biochem. Biophys., 40, 346–351 (1952)), followed by measurement of the dissolved area (mm²) of the fibrin membrane 18 hours later, wherein fibrinogen used for the preparation of the standard fibrin plate was of bovine origin as produced by Dai-Ichi Kagaku Yakuhin Co. of Japan) and thrombin used was of bovine origin as manufactured by Mochida Pharmaceuticals Co. of Japan). Fibrin and fibrinogen degradation products (hereinafter referred to briefly as "FDP") were determined by use of the latex coagulation method based on the FDPL test of Teikoku Hormone Mnfg. Co. of Japan); a sample serum was diluted 1 to 32 fold with a diluent for the sample as specified in the attached instructions for use, and 0.07 ml of the diluted solution was admixed with 0.04 ml of latex reagent and stirred on a slide plate, followed by observation for coagulation 2 min later (for example, when coagulation took place with a two-fold diluted solution of the serum, the FDP concentration was taken as 1 μg/ml, and in the case of occurrence of coagulation with a 4-fold diluted solution, the FDP concentration as 2 μg/ml).

The plasma TPA activity was expressed in terms of an amount of produced antigen as determined against the human melanoma TPA (ng/ml) in accordance with the method of Bergsdorf (N. Bergsdorf et al.: Thromb. Haemostats., 50, 740–744 (1983)) while using the ELISA kit manufactured by Blopool Co. of U.S.A.).

The measurement results are shown in Table 2, which indicates that administration of NK caused gradual increase in EFA(A) over the 1 to 8 hours period and brought about significant elevation in FDP concentration (B) as from Day 1, although it did not produce any appreciable change in WBCLT.

It has also been proved that administration of NK raised progressively a blood level of the antigen against the fibrinolytic enzyme TPA (C) derived from the angioendothelial-X cells which enzyme is at present identified as a factor for the fibrinolytic activity in the blood. The present inventors conducted the same investigation through administration of placebos not containing NK to determine changes both in blood fibrinolytic activity and TPA antigen concentration, and found that placebos did not produce any change.

TABLE 2

Changes of the blood fibrinolytic activity with a number of days elapsed after the administration of subtilisin BPN'

| Subject | Before | Day 1 | Day 2 | Day 4 | Day 8 |
|---|---|---|---|---|---|
| A. WBCLT; | | | | | |
| a | 1200 | 1400 | 970 | 1550 | 1260 |
| b | 310 | 240 | 430 | 280 | 260 |
| c | 160 | 180 | 150 | 230 | 180 |
| d | 530 | 510 | 630 | 490 | 470 |
| e | 220 | 290 | 220 | 230 | 210 |
| N = 5 | 484 ± 424 | 524 ± 505 | 480 ± 332 | 556 ± 566 | 476 ± 453 |
| | | (P < 0.5) | (P < 0.3) | (P < 0.2) | (P < 0.3) |
| B. EFA (mm²); | | | | | |
| a | 0 | 4.2 | 6.5 | 11.6 | 16.4 |
| b | 25.5 | 24.0 | 22.1 | 26.5 | 29.7 |
| c | 19.4 | 25.0 | 26.5 | 32.5 | 33.0 |
| d | 0 | 9. | 19.8 | 14.1 | 7.0 |
| e | 13.3 | 17.6 | 23.0 . | 20.7 | 7.0 |
| N = 5 | 11.6 ± 11.5 | 16.0 ± 9.1 | 19.6 ± 7.7 | 21.1 ± 8.6 | 18.6 ± 12.3 |
| | | (P < | (P < | (P < | (P < |

TABLE 2-continued

Changes of the blood fibrinolytic activity with a number of days elapsed after the administration of subtilisin BPN'

| Subject | Before | Day 1 | Day 2 | Day 4 | Day 8 |
|---|---|---|---|---|---|
| | | 0.5) | 0.3) | 0.2) | 0.3) |
| C. FDP (μg/ml); | | | | | |
| a | 1 | 4 | 8 | 8 | 8 |
| b | 2 | 8 | 4 | 2 | 4 |
| c | 1 | 4 | 8 | 8 | 4 |
| d | 1 | 8 | 4 | 4 | 4 |
| e | 1 | 2 | 2 | 4 | 2 |
| N = 5 | 1.2 ± 0.4 | 5.2 ± 2.7 | 5.2 ± 2.7 | 5.2 ± 2.7 | 4.4 ± 2.2 |
| | | (P < 0.03) | (P < 0.03) | (P < 0.03) | (P < 0.03) |

EXAMPLE 2

Mongrel dogs (male, weighing 10 to 16 kg), which had had experimental thrombus formed through injection of 0.4 ml of 5% bovine fibrinogen and 0.2 ml of 50 units/ml bovine thrombin into the lateral saphena vein according to the procedure of Sasaki et al. (Life Science, 27, 1659–1665 (1980)), were given, orally at once, four enteric-coated capsules (250 mg/capsule) of purified subtilisin BPN' as obtained in Example 1, and after the capsules were allowed to imigrate into the intestinum duodenum, blood samples were collected in the time-course manner to measure the eurogloburin lysis time (ELT) and to conduct X-ray angiography by injecting Angiografin (manufactured by Scherring Co. of West Germany) into the femoral artery at a rate of 4 ml/2 sec. The results indicate that the control group (N=3) being given the capsules not containing the test drug produced no change (P<0.5) in ELT over the period of 0.5 to 12 hours and was observed not to show the artificial thrombus lysis for the period of greater than 18 hours after its formation, whereas the group (N=3) treated through oral administration of the test drug showed shortened lengths of ELT (or intensified activity) after administration of NK, as was evidenced by such measurements as 32±8 min (P<0.02) of ELT 30 min later, 40±10 min (P<0.06) at Hour 1, 42±13 min (P<0.15) at Hour 3 and 53±8 min (P<0.4) at Hour 6. Also, the artificial thrombus was confirmed to undergo complete lysis within 5 hours after administration in the group treated with the test drug, resulting in the finding that oral subtilisin BPN' possesses thrombus lysis effect.

EXAMPLE 3

With subtilisin Carlsberg purchased from Sigma Co. of U.S.A., gel permeation column chromatography on Sephadex G-100 was carried out in the same manner as described in Example 1, and the same experiment as described in Example 1 was conducted with use of the purified product having specific activity of 17 U/mg; the purified enzyme was filled in 0.5 g portions into enteric-coated capsules, and five healthy male adults were given orally the capsules at the daily dose of 3 capsules as divided into three times for the period of 4 days, followed by time-course collection of blood samples to make measurements on the items as mentioned in Example 1. The results are as illustrated graphically in FIG. 1, which indicates that the measurements all were just like those in Example 1, leading to the confirmation that subtilisin Carsberg also can be expected to produce the similar effect.

EXAMPLE 4

By use of the purified subtilisin BPN' as obtained in Example 1, the experiment was carried out but with the varied dosage amount; five healthy male adults were given orally five enteric-coated capsules each containing 1 g of the proteolytic enzyme once a day for the period of 4 days. The number of collection of blood samples and the measurement items were the same as being done in Example 1 to assess the effect.

Shown in Table 3 are the measurement results, which reveal that administration of subtilisin BPN' resulted in gradual elevation of EFA (A) over the period of 1 to 8 hours after administration and also increased significantly the FDP (B) concentration as from Day 1 of administration of NK.

TABLE 3

Time-course changes of the blood fibrinolytic activity after administration of subtilisin BPN'

| Subject | Before | Day 1 | Day 2 | Day 4 | Day 8 |
|---|---|---|---|---|---|
| A. EFA (mm²); | | | | | |
| f | 0 | 9.0 | 27.6 | 22.1 | 22.6 |
| g | 0 | 0 | 9.0 | 25.5 | 16.8 |
| h | 25.0 | 38.4 | 22.1 | 17.6 | 14.4 |
| i | 0 | 14.1 | 18.1 | 23.0 | 17.6 |
| j | 14.8 | 26.5 | 16.4 | 14.4 | 10.2 |
| N = 5 | 10.0 ± 12.2 | 17.6 ± 15.1 | 18.6 ± 6.9 | 20.5 ± 4.5 | 16.3 ± 4.5 |
| | | (P < 0.3) | (P < 0.12) | (P < 0.08) | (P < 0.2) |
| B. FDP (μg/ml); | | | | | |
| f | 1 | 4 | 4 | 8 | 4 |
| g | 2 | 8 | 8 | 4 | 4 |
| h | 2 | 8 | 8 | 4 | 1 |
| i | 1 | 8 | 4 | 8 | 4 |
| j | 1 | 2 | 4 | 2 | 1 |
| N = 5 | 1.4 ± 0.5 | 4.6 ± 1.9 | 5.6 ± 2.2 | 5.2 ± 2.7 | 2.8 ± 1.6 |
| | | (P < 0.05) | (P < 0.004) | (P < 0.04) | (P < 0.15) |
| C. TPA (ng/ml); | | | | | |
| f | 6.2 | 9.3 | 10.5 | 8.3 | 8.5 |
| g | 5.1 | 6.6 | 8.3 | 7.3 | 5.9 |
| h | 8.8 | 10.7 | 10.2 | 11.5 | 9.8 |
| i | 3.9 | 6.1 | 7.9 | 9.9 | 10.2 |
| j | 7.1 | 8.1 | 7.1 | 11.3 | 7.3 |
| N = 5 | 6.2 ± 1.9 | 8.2 ± 1.9 | 8.8 ± 1.5 | 9.7 ± 1.8 | 8.3 ± 1.3 |
| | | (P < 0.15) | (P < 0.05) | (P < 0.02) | (P < 0.11) |

EXAMPLE 5

A cultivation product of Bacillus amyloliquesiens was purified by use of the method of D. Tsuruta et al. as stated herein and further treated for purification through gel permeation column chromatography (5 cm°×90 cm) on Butyl Sepharose (400 ml) and Sephadex G-100 under the same chromatographic conditions as described in Example 1 to give 10 g of of the purified subtilisin amylosachariticus. A cultivation product of Bacillus amyloliquesiens was purified by use of the method of D. Tsuruta et al. as described herein and further treated for purification through gel permeation column chromatography (5 mm°×90 cm) on Butyl Sepharose (400 ml) and Sephadex G-100 under the same chromatographic conditions as described in Example 1 to give 10 g of the purified subtilisin amylosachariticus. The administration experiment was conducted in the same manner as mentioned in Example 1; namely, the subjects were given orally three enteric-coated capsules containing 0.05 g of the purified enzyme, as divided into three times, for the period of 8 consecutive days, followed by collection of blood samples at the same interval as stated in Example 1 to measure the EFA, FDP and TPA values.

Their measurements as taken in the time-course manner are shown in Table 4, which indicates that subtilisin amylosacchariticus, when administered orally, also produced the effect on the fibrinolytic system nearly identical to the case with subtilisin BPN' of Example 1.

TABLE 4

Time-course changes of the blood fibinolytic activity after administration of subtilisin amylosacchariticus

| Subject | Before | Day 1 | Day 2 | Day 4 | Day 8 |
|---|---|---|---|---|---|
| A. EFA (mm$^2$); | | | | | |
| k | 10.2 | 20.2 | 21.2 | 17.6 | 14.4 |
| l | 0 | 10.2 | 11.9 | 14.8 | 16.8 |
| m | 0 | 0 | 6.3 | 16.0 | 11.6 |
| n | 18.5 | 15.2 | 18.1 | 17.2 | 14.1 |
| o | 10.2 | 15.2 | 17.2 | 9.3 | 0 |
| N = 5 | 7.8 ± 7.9 | 12.2 ± 9.7 (P < 0.27) | 14.9 ± 5.9 (P < 0.15) | 15.0 ± 3.4 (P < 0.12) | 11.4 ± 6.6 (P < 0.5) |
| B. FDP (μg/ml); | | | | | |
| k | 2 | 2 | 4 | 8 | 4 |
| l | 1 | 8 | 4 | 2 | 2 |
| m | 1 | 2 | 8 | 4 | 2 |
| n | 1 | 4 | 8 | 8 | 2 |
| o | 1 | 4 | 4 | 2 | 1 |
| N = 5 | 1.2 ± 0.4 | 4.0 ± 2.4 (P < 0.07) | 5.2 ± 2.7 (P < 0.03) | 4.0 ± 2.4 (P < 0.07) | 2.2 ± 1.1 (P < 0.12) |
| C. TPA (ng/ml); | | | | | |
| k | 12.0 | 11.8 | 14.2 | 12.8 | 11.6 |
| l | 5.1 | 7.8 | 8.9 | 8.8 | 6.9 |
| m | 8.3 | 9.3 | 9.6 | 9.3 | 8.8 |
| n | 6.8 | 7.9 | 9.1 | 9.8 | 8.8 |
| o | 9.1 | 9.4 | 10.3 | 11.8 | 9.8 |
| N = 5 | 8.3 ± 2.6 | 9.2 ± 1.6 (P < 0.5) | 10.4 ± 2.2 (P < 0.2) | 10.5 ± 1.7 (P < 0.15) | 9.2 ± 1.7 (P < 0.5) |

EXAMPLE 6

The same experiment as described in Example 2 was carried out with use of the purified subtilisin Carlsberg as obtained in Example 3; namely, each of adult mongrel dogs (male weighing from 10 to 16 kg), which had had artificial thrombus formed through injecting 0.4 ml of 5% bovine fibrinogen and 0.2 ml of 50 units/ml bovine thrombin into hte lateral saphena vein according to the procedure of K. Sasaki et al. (Life Science, 27, 1659–1665 (1980)), were given orally four enteric-coated capsules containing subtilisin Carlsberg (250 mg/capsule) at once which were prepared by the same procedure as described in Example 1, and after the capsules imigrated into the intestinum duodenum, blood samples were drawn in the time-course manner to measure the eurogloburin lysis time (ELT) in accordance with the previously mentioned procedure of K. Sasaki et al. and also to conduct X-ray angiography by injecting Angiografin (produced by Scherring Co. of West Germany) into the main artery of the inguinal region at a rate of 4 ml/2 sec. The results are shown in Table 5, which indicates that the control group (N=3) receiving the capsules not containing the test drug produced no change (p 0.5) in ELT over the period of 0.5 to 12 hours after administration and was observed not to cause any lysis of the artificial thrombus for the period of not less than 18 hours after its formation, whereas the group treated through administration of the test drug showed shortened lengths of ELT (or intensified lysis activity) over the period of 0.5 to 6 hours after administration. In the group treated with the test drug, the artificial thrombus was observed in every cases to undergo lysis within 5 hours within 5 hours after its formation. TYhe above findings led to the confirmation that subtilisin Carlsberg possesses thrombus lyzing activity.

TABLE 5

Time-course changes of ELT in the thrombus models (dogs) treated through oral administration of subtilisin Carlsberg

| Subject | Before | 0.5 hr | 1 hr | 3 hr | 6 hr |
|---|---|---|---|---|---|
| | 70 | 35 | 45 | 50 | 60 |
| | 50 | 25 | 50 | 55 | 55 |
| | 65 | 30 | 45 | 35 | 45 |
| | 62 ± 10 | 30 ± 5 (p < 0.01) | 47 ± 3 (P < 0.15) | 47 ± 10 (P < 0.2) | 55 ± 10 (P < 0.4) |

We claim:

1. A method for treating thrombosis in a patient in need thereof comprising administering orally to said patient a therapeutically effective amount of a proteolytic subtilisin enzyme isolated from a microorganism of the genus Bacillus.

2. The method for treating thrombosis as claimed in claim 1, wherein the microorganism is *Bacillus subtilis, Bacillus licheniformis* or *Bacillus amyloliquefaciens.*

3. The method for treating thrombosis as claimed in claim 1, wherein the proteolytic subtilisin enzyme is subtilisin BPN', subtilisin Carsberg or subtilisin amylosacchariticus.

4. The method for treating thrombosis as claimed in claim 1, wherein the proteolytic subtilisin enzyme is administered orally to the patient in a daily dosage of 0.02 to 2 g.

5. The method for treating thrombosis as claimed in claim 1, wherein the proteolytic subtilisin enzyme is administered as an enteric preparation.

6. The method for treating thrombosis as claimed in claim 1, wherein the proteolytic subtilisin enzyme is administered orally to said patient in a daily dosage of 0.05 to 1 g.

* * * * *